(12) United States Patent
Pinel

(10) Patent No.: US 8,181,651 B2
(45) Date of Patent: May 22, 2012

(54) HAND POWERED SUCTION DEVICE WITH MUCUS TRAP AND SUCTION CATHETER FOR TRACHEOSTOMY TUBES

(75) Inventor: Lloyd Jay Pinel, Third Lake, IL (US)

(73) Assignee: Passy-Muir, Inc., Irvine, CA (US)

( * ) Notice: Subject to any disclaimer, the term of this patent is extended or adjusted under 35 U.S.C. 154(b) by 970 days.

(21) Appl. No.: 12/220,089

(22) Filed: Jul. 22, 2008

(65) Prior Publication Data

US 2009/0025717 A1   Jan. 29, 2009

Related U.S. Application Data

(60) Provisional application No. 60/961,748, filed on Jul. 24, 2007.

(51) Int. Cl.
    A61M 16/00   (2006.01)
(52) U.S. Cl. .......... 128/205.19; 604/317; 604/540
(58) Field of Classification Search .......... 128/205.19; 604/11, 218, 73, 75, 36, 37
    See application file for complete search history.

(56) References Cited

U.S. PATENT DOCUMENTS

| | | | | |
|---|---|---|---|---|
| 1,022,601 A | * | 4/1912 | Rumberg et al. | 604/30 |
| 1,481,008 A | * | 1/1924 | Hodlick | 604/212 |
| 1,526,313 A | * | 2/1925 | Blakeslee | 604/37 |
| 2,511,469 A | * | 6/1950 | Hawks | 604/185 |
| 2,612,894 A | * | 10/1952 | Akins | 604/212 |
| 2,672,141 A | * | 3/1954 | Filger | 128/200.22 |
| 2,890,699 A | * | 6/1959 | Miller | 604/213 |
| 3,017,880 A | * | 1/1962 | Brook | 128/203.11 |
| 3,223,289 A | * | 12/1965 | Bouet | 222/209 |
| 3,333,844 A | * | 8/1967 | Jurschak | 482/13 |
| 3,651,808 A | * | 3/1972 | White | 604/213 |
| 4,078,588 A | * | 3/1978 | Hardwick | 141/59 |
| 4,102,342 A | * | 7/1978 | Akiyama et al. | 606/192 |
| 4,258,714 A | * | 3/1981 | Leopoldi et al. | 604/118 |
| 4,299,215 A | * | 11/1981 | Anon | 128/200.24 |
| 4,386,607 A | * | 6/1983 | Miller | 604/37 |
| 4,397,643 A | * | 8/1983 | Rygiel | 604/317 |
| 4,684,362 A | * | 8/1987 | Holt | 604/540 |
| 4,709,705 A | * | 12/1987 | Truglio | 600/563 |
| 4,790,818 A | * | 12/1988 | DeLuca et al. | 604/540 |
| 4,801,292 A | * | 1/1989 | Watson | 604/36 |
| 4,805,611 A | * | 2/1989 | Hodgkins | 128/207.14 |
| 4,817,626 A | * | 4/1989 | Blaine | 600/541 |
| 4,825,859 A | * | 5/1989 | Lambert | 128/202.16 |
| 5,050,616 A | * | 9/1991 | Wolff et al. | 600/573 |
| 5,098,418 A | * | 3/1992 | Maitz et al. | 604/319 |
| 5,290,257 A | * | 3/1994 | Zhong | 604/212 |

(Continued)

FOREIGN PATENT DOCUMENTS

EP    451062   * 10/1991   ............ 604/133

(Continued)

*Primary Examiner* — Loan Thanh
*Assistant Examiner* — Shila Jalalzadeh Abyane
(74) *Attorney, Agent, or Firm* — Knobbe, Martens, Olson & Bear, LLP

(57) ABSTRACT

A device and method for suctioning mucus and secretions from a patient's tracheostomy tube is described. The device utilizes a reusable squeezable bulb with check valves to regulate air flow in and out of the squeezable bulb and a disposable mucus trap and suction catheter to suction a tracheostomy tube effectively and discretely without using an electrically powered suction machine.

10 Claims, 3 Drawing Sheets

U.S. PATENT DOCUMENTS

| | | | |
|---|---|---|---|
| 5,318,510 A * | 6/1994 | Cathcart | 604/6.09 |
| 5,342,329 A * | 8/1994 | Croquevielle | 604/319 |
| 5,398,674 A * | 3/1995 | Martin | 128/203.11 |
| 5,643,202 A * | 7/1997 | Gravenstein et al. | 604/514 |
| 5,702,362 A * | 12/1997 | Herold et al. | 604/58 |
| 5,848,993 A * | 12/1998 | Tanhehco et al. | 604/217 |
| 6,138,668 A * | 10/2000 | Patton et al. | 128/200.14 |
| 6,167,699 B1 * | 1/2001 | Johnston et al. | 60/304 |
| 6,263,875 B1 * | 7/2001 | Pace et al. | 128/207.18 |
| 6,290,667 B1 * | 9/2001 | Cook | 604/19 |
| 6,595,949 B1 * | 7/2003 | Shapiro | 604/73 |
| 6,725,568 B2 * | 4/2004 | Gronka | 34/437 |
| 6,907,879 B2 * | 6/2005 | Drinan et al. | 128/202.22 |
| 7,300,424 B1 * | 11/2007 | Mulford | 604/319 |
| 7,862,548 B2 * | 1/2011 | Javer et al. | 604/310 |
| 2002/0058915 A1 * | 5/2002 | Wakabayashi | 604/319 |
| 2003/0181886 A1 * | 9/2003 | Negron | 604/514 |
| 2007/0270736 A1 * | 11/2007 | Giarrocco-Brettner | 604/37 |
| 2009/0281454 A1 * | 11/2009 | Baker et al. | 600/573 |
| 2010/0114016 A1 * | 5/2010 | Gallo et al. | 604/73 |

FOREIGN PATENT DOCUMENTS

WO     WO 9003194 A1 *    4/1990

* cited by examiner

HAND POWERED SUCTION DEVICE WITH MUCUS TRAP AND SUCTION CATHETER FOR TRACHEOSTOMY TUBES

CROSS-REFERENCE TO RELATED APPLICATIONS

This application claims the benefit of provisional application No. 60/961748 filed Jul. 24, 2007.

STATEMENT REGARDING FEDERALLY SPONSORED RESEARCH OR DEVELOPMENT n/a

REFERENCE TO SEQUENCE LISTING n/a

BACKGROUND OF THE INVENTION

This invention relates to the field of medical care, specifically the suctioning of tracheostomy tubes. There are many patients in the U.S. who, for various reasons require a tracheostomy tube in order to maintain their airway. A tracheostomy tube is a short curved tube inserted through a surgical hole in the patient's neck, and held in place with a tracheostomy tie around the patient's neck. Patients, who have a tracheostomy tube need to have their tracheostomy tube suctioned on a regular basis, typically once per hour, or more often when the patient is sick or other circumstances dictate. Suctioning a tracheostomy tube is necessary to remove mucus and secretions from the tube. This suctioning is typically accomplished using an electrically powered suction machine. Patients in care facilities or hospitals always have an electrically powered suction machine at the bedside. Other patients with tracheostomy tubes are mobile and are out in public places, or are cared for at home, without access to an electrically powered suction machine.

Even for patients with access to an electrically powered suction machine, there are several reasons that a patient may benefit from having a non-electrical suction device available. Many times the patient does not require much suctioning but only needs to have a small amount of secretions or mucus removed from the tracheostomy tube.

Suctioning a patient with an electrically powered suction machine in public places draws unwanted attention to the patient due to the noise which the suction machine makes.

Suction which is more aggressive than is necessary causes many problems for the patient. Electrically powered suction machines have many mechanical, electrical, and somewhat fragile plastic components, and therefore can and do stop working, when this occurs having a hand held hand powered suction device available as a back-up could be extremely valuable.

There are only two types of devices currently available which do not rely on electricity to provide suction for tracheostomy tubes: (1) a bulb syringe of the type used to suction a newborns mouth and nose, and (2) a handheld rescue suction device, the most common one known as a V-Vac. The first does not work well for tracheostomy tubes because there is no catheter to reach into the tracheostomy tube and the mucus and secretions are not retained in the bulb syringe between each suctioning. The second type is used by emergency responders. This device is designed for suctioning vomit and secretions from a patient's mouth. This type of device is fairly large, and the disposable containers which it uses are expensive to replace. Also this device creates more suction than is normally required for suctioning a tracheostomy tube. Neither of these devices have a selection of suction catheters available which would work well with tracheostomy tubes.

Therefore, there is a need for a small portable device, capable of suctioning a tracheostomy tube without the need for, or in addition to, an electrically powered suction machine.

BRIEF SUMMARY OF THE INVENTION

In view of the aforementioned, it is a primary object of the present invention to provide an improved bulb syringe type suction device designed specifically for use with tracheostomy tubes.

This suction device utilizes one way check valves along with a baffle/trap to allow the device to create suction when the bulb is released and contain the suctioned material inside the device when the bulb is squeezed in order to continue suctioning as necessary.

Another object of the invention is to provide a suction device which is small and compact enough to be stored in the patient's suction machine bag in order to be used if the suction machine breaks or malfunctions.

Another object of the invention is to provide a non-electrically powered suction device which is economical to produce, economical to replace disposable parts, and is easy to clean.

Another object of the invention is to provide a suction device which operates more quietly and less obtrusively than available electrically powered suction devices, for use in public places.

These and other objects of the present invention will become apparent to those skilled in the art from the drawings and the following description.

DETAILED DESCRIPTION OF THE INVENTION

Figure 1:
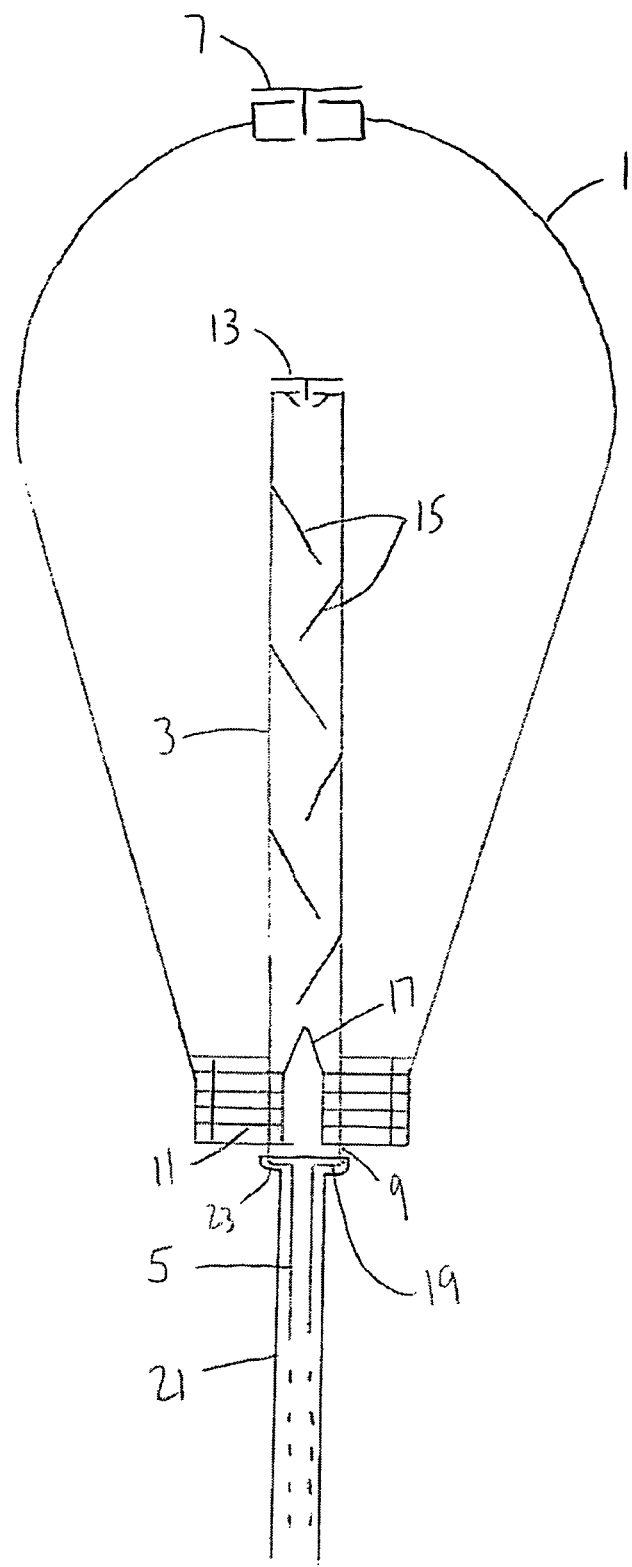
FIG. 1 is a schematic representation of the preferred embodiment of the present invention.

Referring generally to FIG. 1, the device consist of two general parts groups; 1) the squeezable bulb 1 which is reusable and 2) the mucus trap 3 and suction catheter 5 which may or may not be disposable. The mucus trap 3 and suction catheter 5 are detachable from the squeezable bulb 1, and further can be made of two separate parts, where the suction catheter 5 can be attached and detached from the mucus trap 3.

The squeezable bulb 1 is preferably approximately four inches in diameter by six inches long; however, it should be made of a size that will comfortably be used by an average sized adult's hand. The bulb portion can be made of rubber, plastic, or any combination of materials which allow it to be flexible enough to be squeezed and released repeatedly, and elastic enough that it will return to its original shape when it is released. The material preferably should also be resistant to moisture and be able to withstand repeated washing and cleaning without degrading. The shape of the squeezable bulb can take many forms including; round, oblong, or even the shape of a child's toy for pediatric use. There is an exhaust valve 7 shown at the larger end of the squeezable bulb 1, this exhaust valve 7 is a one-way valve which allows air inside of the bulb to be exhausted to the ambient air when the bulb is collapsed by squeezing. This exhaust valve 7 can be of any type including, but not limited to; duckbill check valve, spring loaded ball check valve, mushroom valve, or flap valve. This valve can be made of plastic, rubber, metal, or any other material that is suitable. This exhaust valve 7 may or may not be fitted with a filter (not shown). This exhaust valve 7 may be placed anywhere on the squeezable bulb 1 so long as it does not interfere with the use of the device.

The opposite end of the squeezable bulb 1 from the exhaust valve 7 as shown in the drawing is an opening 9. This opening 9 can be round, square, or any other shape. This opening 9 has a means 11 of accepting and holding firmly or locking in place the mucus trap 3 and suction catheter 5. The means 11 of accepting and holding the mucus trap 3 and suction catheter 5 can be but is not limited to; coarse threads, fine threads, ridges, compression fitting, and pressure fit. In the Figure, a representation of coarse threads is shown as the means 11.

The mucus trap 3 is positioned inside of the squeezable bulb 1 and is held in place in the opening 9 by means 11 including but not limited to; coarse threads, fine threads, ridges, compression fitting, or pressure fit. The mucus trap 3 can be made of any appropriate material including but not limited to; plastic, rubber, metal or composite material. The shape of the mucus trap 3 can include but is not limited to; cylindrical, rectangular, hexagonal or round. The size of the mucus trap 3 can vary, however it should be large enough to hold a reasonable quantity of mucus or secretions, but small enough to not adversely affect the working volume of the squeezable bulb 1. There is a one-way valve 13 shown at the end of the mucus trap 3 opposite the end which the suction catheter 5 attaches. This valve 13 type can be but is not limited to; duckbill check valve, spring loaded ball check valve, mushroom valve or flap valve. Although this valve 13 is shown at the end of the cylindrical mucus trap 3, it may be located in various positions including the side, top or bottom, so long as it is positioned toward the opposite end of the mucus trap 3 from the suction catheter 5.

Inside of the mucus trap 3 is shown a system of baffles 15. Shown in the Figure, the baffles 15 are preferably straight, angled away from the valve 13, and at regular lengths, positions, and angles. However, each of these characteristics of the baffles 15 can be changed. For example, the baffles 15 may be irregular in shape, size, position, and angle. The baffles 15 may be round, star-shaped, curved, or any other suitable shape. They may have holes, openings, or any other feature which may help trap mucus and other fluids, while allowing air to flow through the mucus trap.

The mucus trap 3 includes a one way valve 17 positioned at the end nearest the suction catheter 5. This valve 17 type can be but is not limited to; duckbill check valve, spring loaded ball check valve, mushroom valve or flap valve.

The mucus trap 3 assembly also includes a projection 19 on the outside of the opening 9 of the squeezable bulb 1 which allows a rigid cover 21 to be secured to the projection 19 for the protection of the suction catheter 5. This cover 21 can be secured to the projection 19 by several methods including but not limited to; coarse threads, fine threads, ridges, or pressure fit. The cover 21 is preferably generally cylindrical and hollow, for the suction catheter 5 to fit inside.

This particular embodiment of the cover 21 shown in FIG. 1 has a flange 23 which pressure fits over the projection 19.

The mucus trap 3 assembly further includes a suction catheter 5. This suction catheter 5 can be either joined permanently to the mucus trap 3 or may be detachable from the mucus trap 3. This suction catheter 5 can be made in various sizes as required for various sized tracheostomy tubes. This suction catheter 5 can be made of various types of materials, including but not limited to; plastic, rubber or silicone.

Description of Operation

Figure 2:
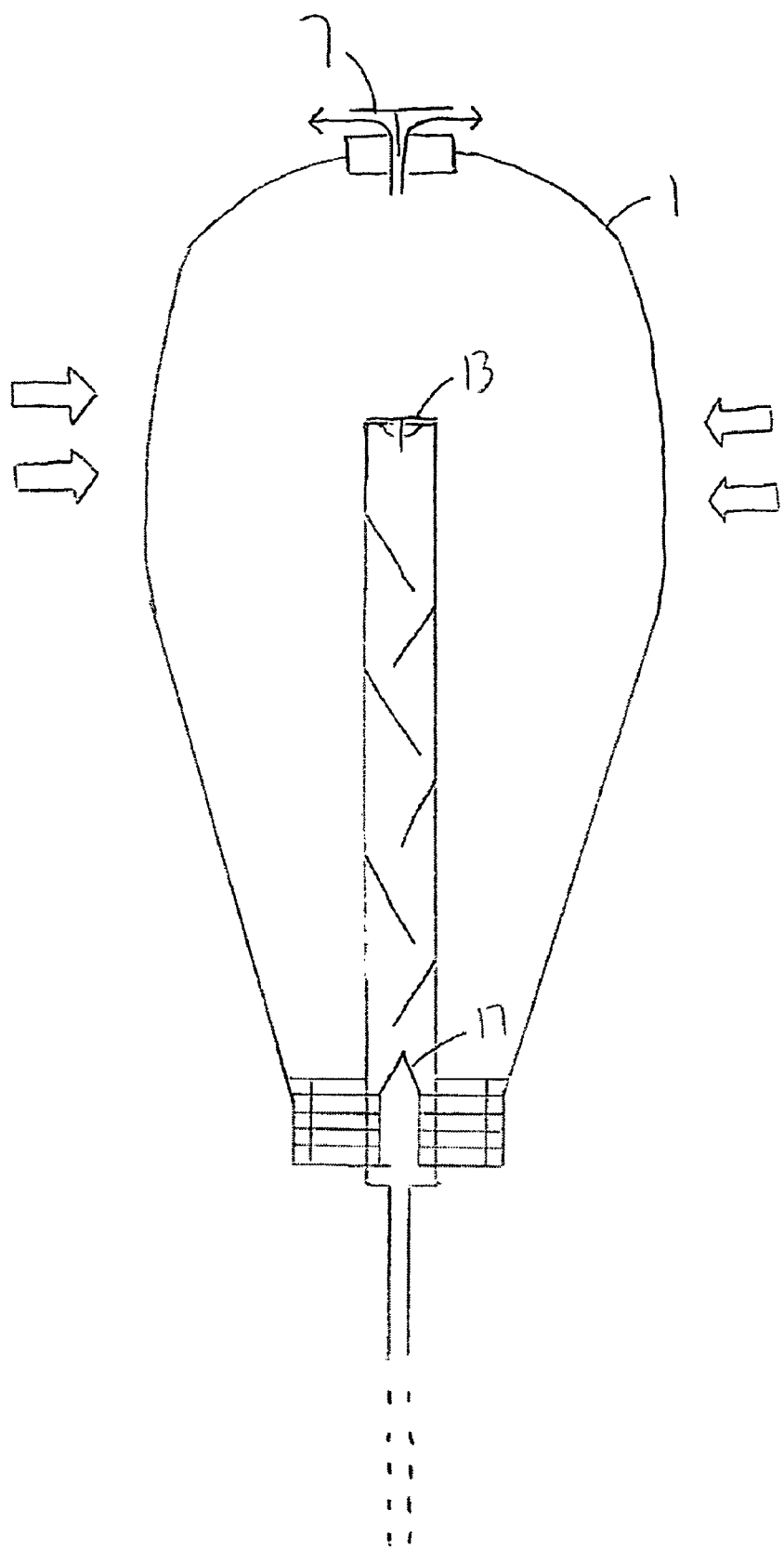
FIG. 2 is a diagram of the operation of the preferred embodiment of the present invention when squeezed.
Figure 3:
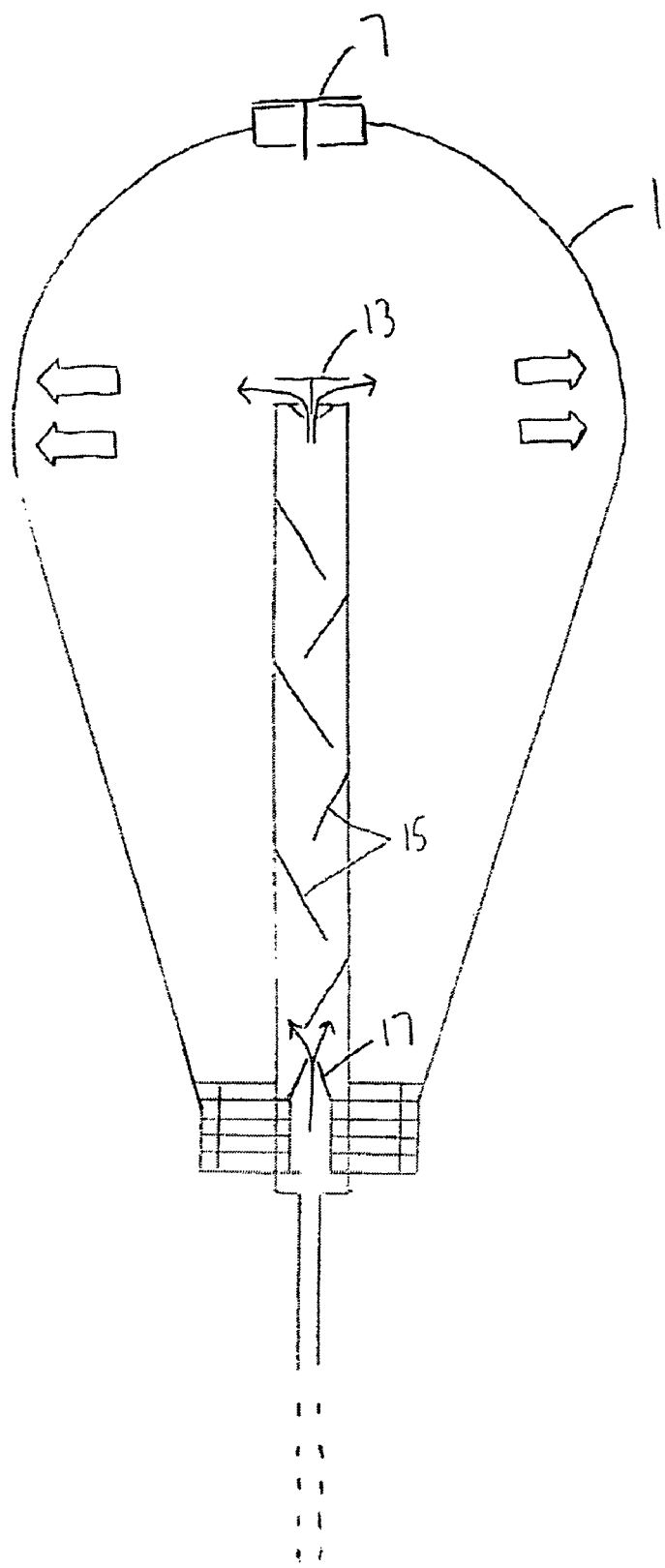
FIG. 3 is a diagram of the operation of the preferred embodiment of the present invention when squeezing pressure is released.

FIGS. 2 and 3 show the operation of the device when squeezed (FIG. 2) and released (FIG. 3). Referring to FIG. 2, when the squeezable bulb 1 is squeezed in preparation for suctioning, the air inside the bulb 1 is forced out of the bulb 1 through the one-way valve 7, as depicted by the arrows. The one-way valve 13 and the one-way valve 17 prevent air and secretions from being forced out through the mucus trap 3 and suction catheter 5. Referring to FIG. 3, a vacuum is created inside the squeezable bulb 1 as the bulb 1 is released and returns to its original shape. Air being drawn into the bulb 1 enters through the one-way valve 17 and one-way valve 13, creating the suction needed to remove mucus and secretions from the tracheostomy tube. The air and secretions move through the one-way valve 17 and into the mucus trap 3. The baffles 15 allow the air to flow through the mucus trap 3 and into the squeezable bulb 1, but help to keep the mucus contained within the mucus trap 3. Air is not allowed out of the squeezable bulb 1 through the valve 7. The bulb 1 can be repeatedly squeezed and released to create the required amount of suctioning. The mucus trap 3 and suction catheter 5 can preferably be replaced every 24 hours or more often if necessary. The squeezable bulb 1 preferably can be cleaned and reused.

The suction device should be carried in the same bag as the suction machine, and would include a rigid plastic cover 21 for the suction catheter 5 which would keep the suction catheter 5 clean.

The disposable mucus trap 3 and suction catheter 5 will be produced in various sizes, corresponding to tracheostomy tube sizes ranging from neonatal to adult sizes.

Because the device is designed to be used with tracheostomy tubes and not with endotracheal tubes, the suction catheter 5 is preferably only slightly longer than the typical tracheostomy tube length. This, combined with the limited vacuum created by this type of device compared with an electrically powered suction machine, limits the problem of excessive and aggressive deep suctioning so commonly seen in care facilities. This will be a benefit to patients with tracheostomy tubes because excessive and unnecessary deep suctioning causes trauma, bleeding, infection, scarring and other problems.

In accordance with the provisions of the patent statutes, the present invention has been described in what is considered to represent its preferred embodiment. However, it should be noted that the invention can be practiced otherwise than as specifically illustrated and described without departing from its spirit and scope.

What I claim is:

1. A device for clearing a tracheostomy tube, comprising:
   a squeezable bulb having a first end and a second end, the second end disposed to provide suction to a tracheostomy tube when squeezing pressure is released from said squeezable bulb;
   a first one-way valve disposed at said first end of said squeezable bulb, to allow air to escape from said squeezable bulb when squeezing pressure is applied to said squeezable bulb;
   a mucus trap disposed within said squeezable bulb;
   a plurality of baffles disposed within said mucus trap, to trap mucus and other secretions within said mucus trap;

a second one-way valve disposed on said mucus trap and at said second end of said squeezable bulb; and a suction catheter attached to said mucus trap and partially disposed within the tracheostomy tube, wherein mucus and other secretions enter said mucus trap through said suction catheter and said second one-way valve when squeezing pressure is released from said squeezable bulb.

2. A device as in claim 1, wherein said first one-way valve is a check valve.

3. A device as in claim 1, wherein said second one-way valve is a check valve.

4. A device as in claim 1, further comprising a third one-way valve disposed at said first end of said squeezable bulb.

5. A device as in claim 1, wherein the plurality of baffles includes surfaces angled away from the second one-way valve.

6. A device as in claim 1, further comprising a projection configured to be secured to a cover.

7. A device as in claim 1, further comprising a suction catheter in communication with the mucus trap.

8. A suction device comprising:
a squeezable bulb having a proximal end and a distal end, the squeezable bulb including:
a first one-way valve; and
an opening at the distal end;
a mucus trap disposed within the squeezable bulb, the mucus trap having a proximal end and a distal end and including:
a second one-way valve proximate to the proximal end of the mucus trap a third one-way valve proximate to the distal end of the mucus trap; and
a plurality of baffles between the proximal end of the mucus trap and the distal end of the mucus trap, the baffles configured to trap mucus.

9. The device of claim 8, wherein the baffles include straight surfaces angled away from the second one-way valve.

10. The device of claim 8, wherein the opening includes means for locking the mucus trap to the squeezable bulb, the locking means including at least one of coarse threads, fine threads, ridges, compression fitting, and pressure fitting.

* * * * *